(12) United States Patent
Grewal

(10) Patent No.: US 6,861,063 B2
(45) Date of Patent: Mar. 1, 2005

(54) APPLICATION OF PARTIALLY-DESICCATED ENTOMOPATHOGENIC NEMATODES FOR BIOLOGICAL PEST CONTROL

(75) Inventor: Parwinder Grewal, Wooster, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 213 days.

(21) Appl. No.: 09/993,348

(22) Filed: Nov. 19, 2001

(65) Prior Publication Data

US 2002/0094325 A1 Jul. 18, 2002

Related U.S. Application Data

(60) Provisional application No. 60/249,927, filed on Nov. 17, 2000.

(51) Int. Cl.[7] .................. A01N 25/00; A01N 63/00; A01N 65/00
(52) U.S. Cl. ...................... 424/405; 424/93.7
(58) Field of Search ............... 424/405, 93.7; 71/1; 435/410; 504/101, 102, 116.1, 117

(56) References Cited

U.S. PATENT DOCUMENTS

| | | | |
|---|---|---|---|
| 4,002,647 A | 1/1977 | Chodnekar et al. | |
| 4,765,275 A | 8/1988 | Yukawa et al. | |
| 4,983,389 A | 1/1991 | Levy | |
| 4,983,390 A | 1/1991 | Levy | |
| 5,042,427 A | 8/1991 | Bedding | |
| 5,141,744 A | 8/1992 | Chang et al. | |
| 5,183,950 A | 2/1993 | Popiel et al. | |
| 5,989,543 A | 11/1999 | Davide et al. | |
| 6,033,657 A | 3/2000 | Ishibashi | |
| 6,037,378 A | 3/2000 | Grote et al. | |
| 6,043,282 A | 3/2000 | Bayer et al. | |
| 6,130,247 A | 10/2000 | Bayer et al. | |

FOREIGN PATENT DOCUMENTS

| | | |
|---|---|---|
| WO | WO 94-19940 | 9/1994 |

OTHER PUBLICATIONS

Grewal and Georgis, "Entomopathogenic Nematodes," in Methods in Biotechnology, vol. 5: Biopesticides, Use and Delivery (Hall and Mean, Eds.), Humana Press Inc., Totowa, NJ (1999), pp. 271–299.

Georgis et al., "Formulation of Entomopathogenic Nematodes," in Biorational Pest Control Agents: Formulation and Delivery, (Hall and Barry, Eds), American Chemical Society (1995) pp. 197–205.

Anhydrobiotic potential and long–term storage of entomopathogenic nematodes (Rhabditida: Steinernematida ) by Grewal, *International Journal for Parasitology* 30 (2000) 995–1000.

"Enhanced ambient storage stability of an entomopathogenic nematode through anhydrobiosis" by Grewal *Pest Manag Sci* 56:401–406 (2000).

"Osmotic Survival of the Entomopathogenic Nematode Steinernema carpocapsae" by Glazer, et al., *Biological Control* 18, 251–257(2000).

"Desiccation Survival and Water Contents of Entomopathogenic Nematodes, Steinernema spp. (Rhabditida: Steinernematidae)" by Patel, et al., *International Journal for Parasitology*, vol. 27, No. 1, pp. 61–70, 1997.

Primary Examiner—David M. Naff
Assistant Examiner—Deborah K. Ware
(74) Attorney, Agent, or Firm—Calfee, Halter & Griswold LLP

(57) ABSTRACT

Methods for protecting plants from insects are provided. Such methods comprise: applying a formulation comprising partially-desiccated nematodes and a carrier to plant surfaces growing above the surface of the ground (i.e., foliage). Such formulations have a water activity (Aw) of which is less then 0.998 and greater than 0.935. The carrier comprises water and a substance which maintains the water activity of the formulation at levels of from about 0.980 Aw to about 0.940 Aw for a period of 24 hours when the formulation is exposed to air at 70% relative humidity and 25° C. In one embodiment, the carrier is a solution or gel comprising water and a water-retentive polymer. In another embodiment, the carrier is a solution which comprises water and a humectant. In a further embodiment, the formulation comprises both a water-retentive polymer and a humectant. Preferably, the formulation further comprises an ultraviolet (UV) light protectant. In another aspect, the present invention relates to the formulations that are used in such methods.

21 Claims, 7 Drawing Sheets

Fig. 2

Figure 1:
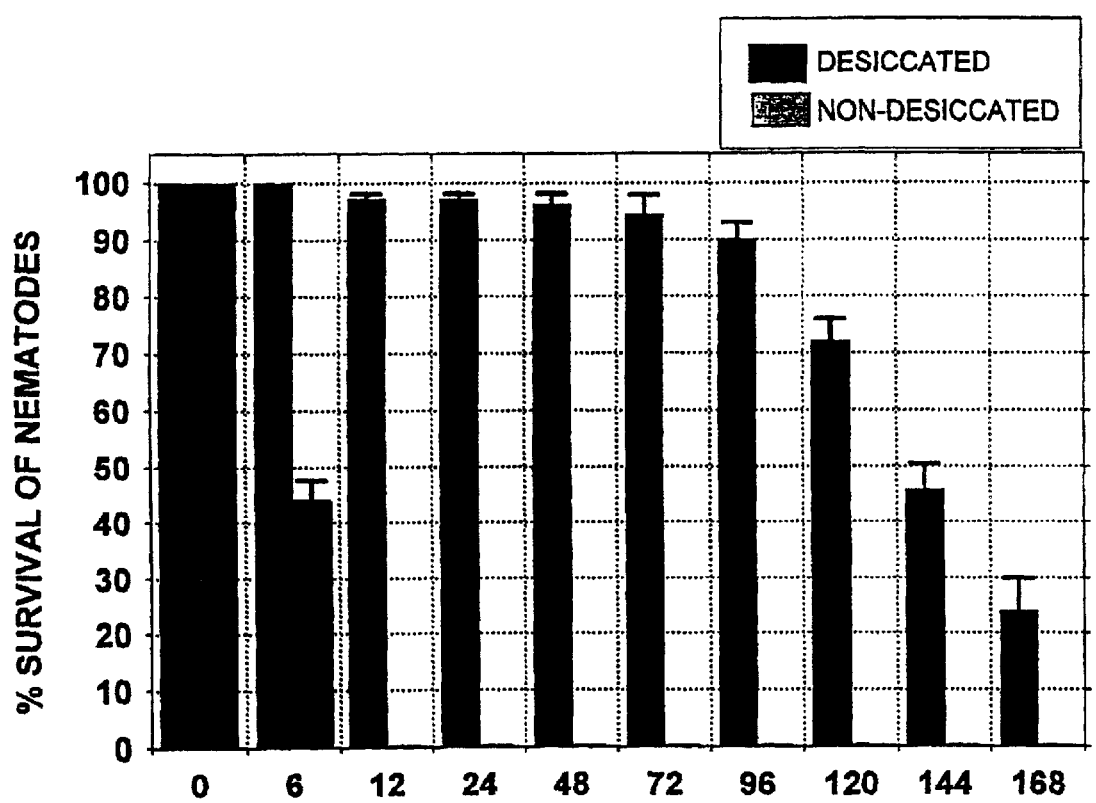

| SPECIES OF INSECT TESTED | CONDITIONING OF NEMATODES | |
|---|---|---|
| | DESICCATED | NON-DESICCATED |
| Trichoplusia ni | 100 ± 0 | 100 ± 0 |
| Helothis verescens | 96.6 ± 3.3 | 100 ± 0 |

APPLICATION OF PARTIALLY-DESICCATED ENTOMOPATHOGENIC NEMATODES FOR BIOLOGICAL PEST CONTROL

CROSS REFERENCE TO RELATED APPLICATIONS

This invention claims priority to U.S. Provisional Patent Application Ser. No.: 60/249,927, filed Nov. 17, 2000.

BACKGROUND

An important agricultural issue is management of crop-destroying insects. Use of chemical pesticides is the primary solution for controlling insects and, in 1999, more than 200 million tons of such pesticides were applied in the US. Unfortunately, use of chemical pesticides is a potential cause of health and environmental problems, especially if the pesticides get into the soil and water supply.

Concern over the potential hazards of chemical pesticides has generated interest in alternative approaches for insect pest control. Entomopathogenic nematodes, in the families Steinernematidae and Heterorhabditidae, are lethal insect parasites that have emerged as excellent potential biological control agents for a number of reasons. Entomopathogenic nematodes cause rapid mortality of a broad range of insects. The nematodes are easily mass produced. Entomopathogenic nematodes are also safe for mammals. In fact the US Environmental Protection Agency (EPA) has exempted entomopathogenic steinernematids and heterorhabditids from registration and regulation requirements, thus simplifying considerably the application, development and commercialization of new nematode formulations.

Entomopathogenic nematodes have a symbiotic association (i.e., living together with mutual advantage to both organisms) with bacteria in the family Enterobacteriaceae. The free living stage of the nematodes, called the infective juvenile (IJ) or dauer, seeks out and infects a host insect. Following penetration into the insect, the IJs release the bacteria into the insect blood stream. The bacteria multiply rapidly, killing the insect host within 24–48 hours. Nematodes complete 2–3 generations in the cadaver and new IJs are produced that then leave the insect and seek out new hosts.

Nematodes have been used as insecticides in high value crops, including citrus, cranberries, mushrooms, greenhouse ornamentals, and turfgrasses. The application of these nematodes to soil or plants provides levels of insect control comparable to that of chemical insecticides. The natural habitat of entomopathogenic nematodes is the soil. Nematodes can survive in various conditions of moisture, temperature, texture and chemical composition associated with different soil types. Consequently, nematodes are found on all continents, except Antarctica, and at nearly all latitudes and altitudes. Considered as a group, entomopathogenic nematodes are currently the second most utilized biocontrol agent against insect pests, after *Bacillus thuringiensis*.

Although nematodes are excellent biocontrol agents, their present use has significant limitations. Because the natural habitat of entomopathogenic nematodes is the soil, nematodes are not well adapted to tolerate direct sunlight, ultraviolet (UV) irradiation, or low humidity (i.e.,<80% relative humidity) and can withstand only limited exposure to these conditions. The sensitivity of nematodes to inactivation by extremes of the physical environment prevents them from reaching their full potential as insecticides, in particular when applied to exposed surfaces, such as foliage. Therefore, successful use of nematodes for insect control is currently limited principally to soil or protected environments, where the nematodes are shielded from sunlight and rapid drying.

In summary, although nematode activity on plant foliage is possible, outdoor activity of the infective juvenile nematodes (IJs) on the leaf is limited to several hours because of their inability to withstand the physical environment. This is a situation that is economically unacceptable. Although numerous formulations have been developed to improve the nematode activity on the crop and in storage, major improvements are still very much needed.

SUMMARY OF THE INVENTION

In one aspect, the present invention provides a method for protecting plants from insects. The method comprises: applying a formulation comprising partially-desiccated nematodes and a carrier to plant surfaces growing above the surface of the ground (e.g., foliage). Such formulation has a water activity (Aw) which is less than 0.998. The carrier comprises water and a substance which substantially maintain the water activity of the formulation (i.e. the substance inhibits evaporation of free water from the formulation, and thus, the water activity of the partially-desiccated nematodes, at levels of from about 0.980 Aw to about 0.940 Aw for a period of 24 hours when the formulation is exposed to air at 70% relative humidity and 25° C. In one embodiment, the carrier is a solution or gel comprising water and a water-retentive polymer. In another embodiment, the carrier is a solution which comprises water and a humectant. In a further embodiment, the formulation comprises both a water-retentive polymer and a humectant. Preferably, the formulation further comprises an ultraviolet (UV) light protectant. In another aspect, the present invention relates to the formulations that are used in such methods.

BRIEF DESCRIPTION OF THE FIGURES

FIG. 1. Mean survival of partially-desiccated and fully-hydrated (i.e., non-desiccated) infective juvenile *Steinernema carpocapsae*. The nematodes were partially-desiccated through slow drying in controlled humidity. Nematode survival was determined following 24 hour rehydration in water and was tested at 70% relative humidity at 25° C. Bars indicate standard error.

FIG. 2. Percentage mortality of third instar *Trichoplusia ni* larvae and *Heliothis virescens* larvae fed on cabbage leaf discs treated with partially-desiccated and full-hydrated infective juveniles of *Steinernema carpocapsae.*

FIG. 3. Survival and pathogenicity of partially-desiccated and full-hydrated *Steinernema carpocapsae* sprayed on cabbage plants in a Conviron growth chamber at 80% relative humidity. (A) Survival of the nematodes. (B) Mortality of cabbage looper, *Trichoplusia ni* larvae.

FIG. 4. Survival and pathogenicity of partially-desiccated and fully-hydrated *S. carpocapsae* on potted cabbage plants held out-of-doors. (A) Survival of the nematodes. (B) Mortality of *T. ni* larvae caused by the nematodes. The temperature varied between 68° F. to 98° F. and the relative humidity varied between 60% and 100%. The experiment was initiated at 11:00 AM on Jul. 14, 2000 when there were no clouds in the sky. Nematode survival and pathogenicity against *T. ni* were evaluated as described in Examples 1 and 2. The nematodes were osmotically desiccated in 25% glycerol for two days prior to application.

FIG. 5. Survival of partially-desiccated and fully-hydrated *Steinernema carpocapsae* at 40° C. for different periods. The nematodes were osmotically desiccated in various glycerol concentrations (shown as water activities, Aw) for two days at a concentration of 5,000 nematodes per ml. Samples (100 μl) were taken after 4, 8, and 16 hours of heat treatment, and nematode viability was determined after rehydration in 100 ml of water overnight.

Figure 6:
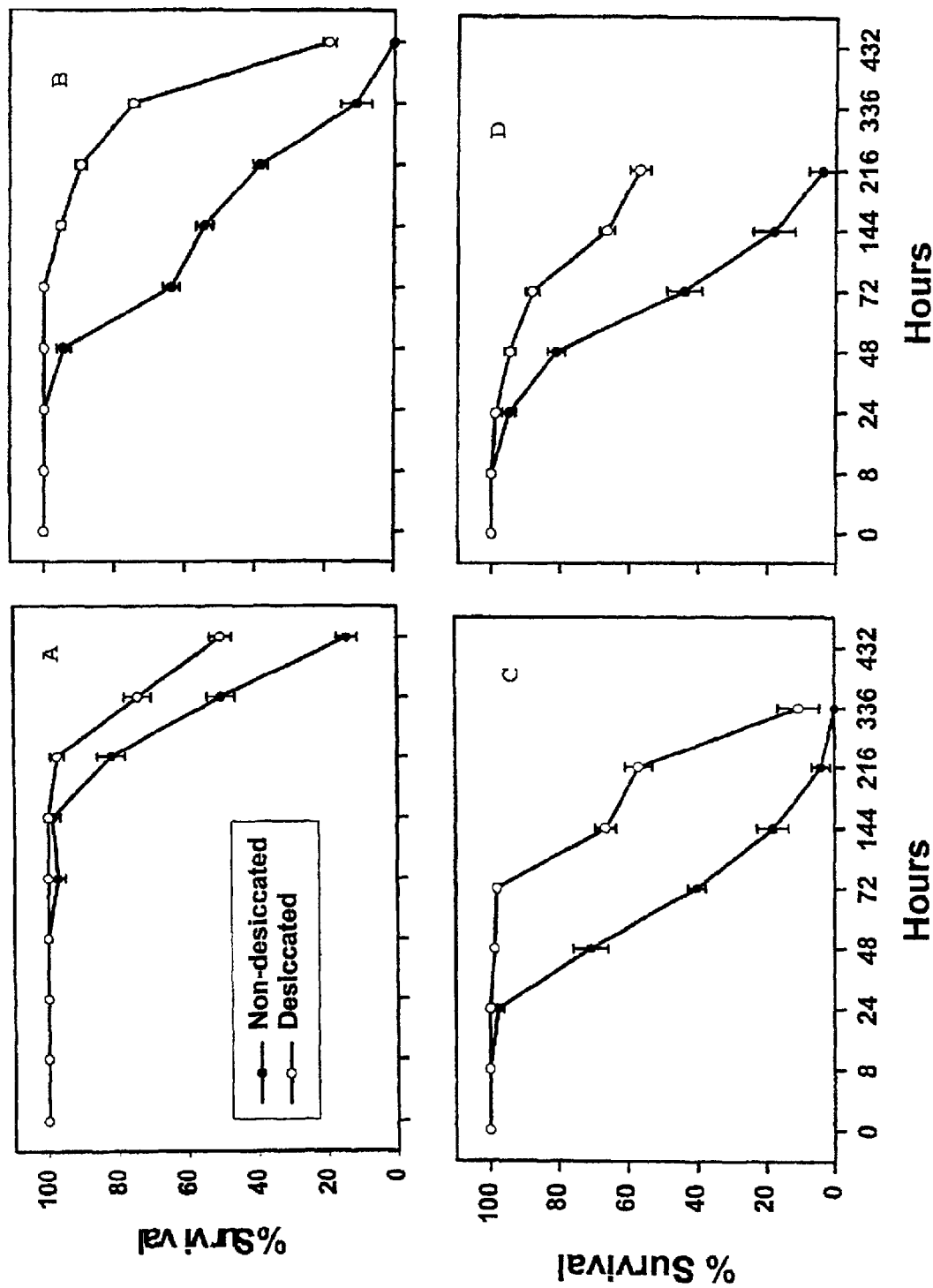

FIG. 6. Enhanced tolerance of partially-desiccated *Steinernema carpocapsae* to additional rapid desiccation. The nematodes were osmotically desiccated in 25% glycerol for two days prior to exposure to different desiccating regimes. The partially-desiccated or fully-hydrated nematodes were then rapidly plunged into different glycerol concentrations and survival was assessed at different intervals by taking 100 μl samples as described in Example 5. The glycerol concentrations were A=30%, B=35%, C=40%, and D=45%.

Figure 7:
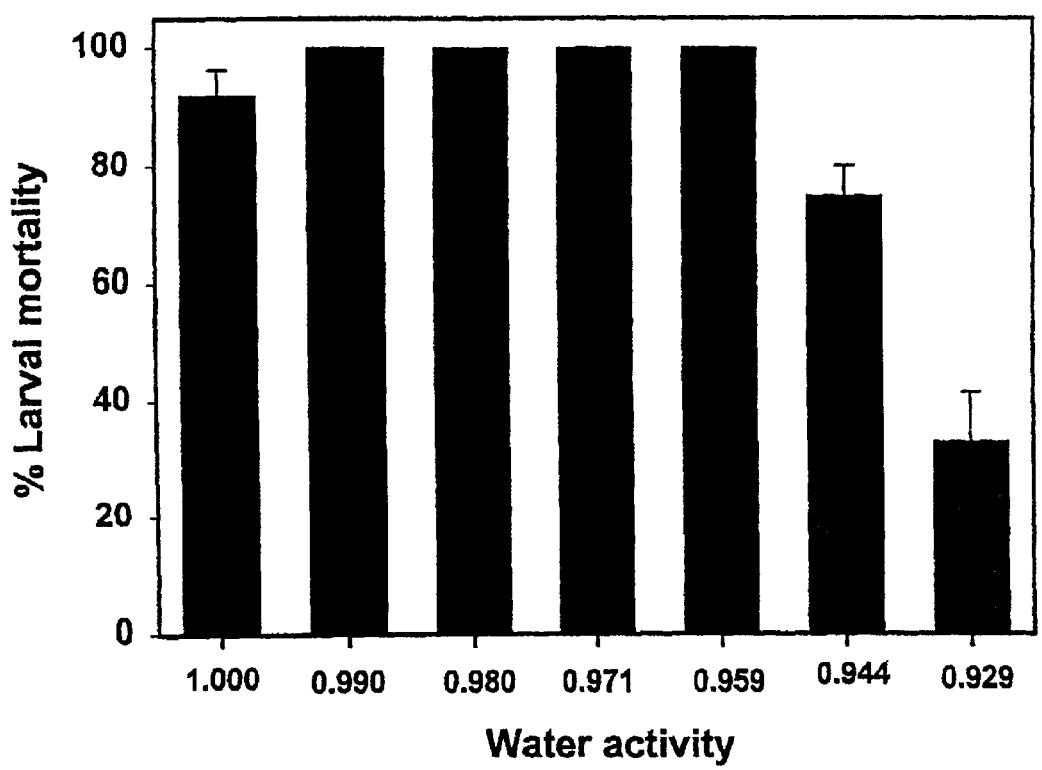

FIG. 7. Mortality of second instar cabbage looper, *Trichoplusia ni* caused by the partially-desiccated or fully-hydrated *Steinernema carpocapsae*. The nematodes were osmotically desiccated in various concentrations of glycerol (shown as water activities) for two days. One 20 μl drop containing 20 nematodes was placed on a 1 cm$^2$ leaf disc placed in a well of a 24-well plate. One second instar *T. ni* larva was placed in each well. The insects were given additional leaf discs (without nematodes) daily. There were four replicates with 12 larvae in each replicate. Final insect mortality was recorded 3 days after the nematodes were applied.

DETAILED DESCRIPTION OF THE INVENTION

Although entomopathogenic nematodes are effective insecticides in protected environments, their effectiveness on foliage is limited because of poor survival due to inability to withstand the physical environment (i.e., conditions of drying and exposure to ultraviolet light). The present invention relates to a method which employs a formulation comprising partially desiccated nematodes and having an Aw less than 0.998 and greater than 0.935, preferably from about 0.980 to about 0.940, to protect plants from infestation by insects. Such formulation further comprises a carrier which comprises water and a substance which maintains the Aw of the formulation and, thus, the nematodes, at a level of from about 0.940 Aw to about 0.980 Aw, during a 24 hour exposure of the formulation to air at 70% relative humidity and 25° C. Such formulation enhances the insecticidal effectiveness of entomopathogenic nematodes on foliage by improving nematode survival in unfavorable environments. In one embodiment, the formulation comprises partially-desiccated nematodes and a gel-forming polymer, preferably a water-retentive polymer. In other embodiments, the formulation comprises a humectant or a combination of humectant and gel-forming polymer. Preferably the formulation further comprises an ultraviolet (UV) light protectant. The formulation is either a liquid or a gel. The method comprises applying the partially-desiccated nematode formulation to plant surfaces growing above the surface of the ground, particularly to plant foliage.

Herein, the term "partially-desiccated nematodes" refers to nematodes having a water activity (Aw) which is from about 0.980 to about 0.940. In accordance with the present invention, it has been shown that nematodes having such Aw survive for 24 hours when exposed to air at 60% to 100% relative humidity and temperatures ranging between 68° and 98° F., and are pathogenic to insects.

Aw is a measure of how tightly water is bound, structurally or chemically, to the nematodes or to the formulation comprising the nematodes. As opposed to water content, Aw is influenced by bonding of water molecules to the surface of substances as well as osmosis. Water activity of the nematodes or the final formulation can be determined using a water activity meter, such as those routinely used in the food industry (e.g., AquaLab Model CX-2, Decagon Devices, Inc., Pullman, Wash.). Such instruments contain a sealed measurement chamber. Aw is defined as the ratio of water vapor pressure in the chamber over a sample (P), e.g. the partially desiccated nematodes or the final formulation, divided by the water pressure over pure water ($P_0$). Thus, multiplication of the water activity of the sample by 100 yields the relative humidity of the atmosphere in equilibrium with the sample.

Through equilibration, viable nematodes (i.e., nematodes that are fully hydrated or are capable of being hydrated) assume the Aw of their surroundings. Thus, viable nematodes achieve an Aw of 1.0 when placed in water for a sufficient amount of time. Similarly, viable nematodes suspended in a solution comprising water and a water-retentive substance, such as for example a solution comprising water and glycerol, assume the Aw of the solution. In addition, viable nematodes maintained in air having a relative humidity of 95% will, after a certain period of time, achieve an Aw of 0.95.

Thus, partially desiccated nematodes can be prepared by incubating viable nematodes in a sealed chamber having a relative humidity of from about 94% to about 98%. Alternatively, partially-desiccated nematodes can be prepared by suspending the viable nematodes in a solution having a water activity of from about 0.940 to about 0.980.

Carriers

In order to prevent the partially-desiccated nematodes from drying out prior to ingestion by the insects, particularly the larvae of the plant insects, viable nematodes are combined with a carrier prior to application to plants. The carriers comprise water and a substance or agent that retards or inhibits evaporation of water and, thus, permit the formulation to substantially maintain a water activity of between 0.980 and 0.940, when exposed to air between 25° C. and 40° C. and a relative humidity below 100%.

In one embodiment, the substance is a water-retentive polymer. The water-retentive polymer is dissolved in water or a water-based solution, such as a buffered solution, and then combined with the partially-dessicated nematodes. Preferably, the water-retentive polymer is a gel-forming polymer. Examples of such gel-forming polymers include, but are not limited to, agarose, carbopols, carrugeenan, dextrin, guar gum and gellan gum. The gel-forming polymers are liquid at room temperature and can be induced to gel by adding a gel inducing agent, such as for example an ion, to the formulation. The gel inducing agent can be added at the time the partially desiccated nematodes are combined with the carrier, or, alternatively later, such as for example, just prior to application of the formulation to the plant. Advantageously, nematodes that are suspended in a water-containing gel are more likely to attach to foliage.

In another embodiment, the substance or agent is a humectant. Humectants, such as for example, glycerol, polyethylene glycol, soluble collagen (Collasol), Folicote, Norbak, sorbitol, Rodspray and Nufilm can be used. Preferably, the humectant reduces evaporation, increases adhesion to foliage, and has little toxicity to the nematodes or insects.

In another embodiment, the formulation comprises both a water-retentive polymer and a humectant.

Other Ingredients Because nematodes are sensitive to UV light, their survival on foliage is decreased by exposure to sunlight. Addition of UV protectants, to the formulation comprising the partially desiccated nematodes and carrier enhances survival of nematodes on exposed foliage. Therefore, UV protectants, preferably, are added to the nematode formation before application to foliage. UV protectants, such as for example, acridine yellow, alkali blue, brilliant yellow, congo red, lissamine green, mercurochrome, methylene blue, benzilidine sulfonic acid, Ulvinul DS49, Erio Acid Red, Raymix and Tinopal can be used.

Application of the Formulation to the Plants

Previous methods for applying partially-desiccated nematodes to plants have employed water-dispersable granules of partially-desiccated nematodes that are first suspended in water to provide a suspension having an Aw of 0.998 to 1.0, and then applied to the soil surrounding the plant or to the foliage of the plant. In accordance with the present invention, it has been determined that rehydration of the partially-desiccated nematodes is not required prior to application. Accordingly, the present formulation, which has an Aw of from about 0.940 to about 0.980, is applied directly to the plants, particularly to the foliage. Preferably, the formulation is applied by spraying the foliage of the plant.

EXAMPLES

The following examples are for purposes of illustration only and are not intended to limit the scope of the claims which are appended hereto.

Example 1

Survivability of Partially Desiccated Nematodes.

Nematodes were partially-desiccated through slow drying in controlled humidity as described in Simons and Poinar (1973) J. Invertebrate Pathology 22: 228–230, which is specifically incorporated herein by reference. Specifically, infective juveniles (IJ) were desiccated on membrane filters at 97% relative humidity in glass desiccators for 12 hours at 25° C. They were then transferred to 93% relative humidity for another 12 hours. Survival of these partially-desiccated nematodes was then compared with that of fully-hydrated (i.e., non-desiccated) infective juveniles. Samples of the partially-desiccated and non-desiccated nematodes were transferred to a 70% relative humidity environment and assayed after 6, 12, and 24 hours, then every 24 hours until 7 days. Nematode viability was determined after hydrating the nematodes in water for 24 hours. Nonmobile nematodes were probed to confirm viability. The partially-desiccated nematodes survived for more than 7 days at 70% relative humidity, whereas the fully-hydrated nematodes perished within 6–12 hours (FIG. 1).

Example 2

Infectivity of the Partially Desiccated Nematodes of Example 1

The infectivity of the partially desiccated nematodes of example 1 against the cabbage looper, *Trichoplusia ni*, and tobacco budworm, *Heliothis virescens*, was determined using a cabbage leaf disc bioassay. Nematodes were partially desiccated as described in Example 1 (Aw 0.944). The partially desiccated nematodes were suspended in a 25% glycerol solution (Aw=0.944). A formulation comprising 100 partially-desiccated nematodes in 20 µl of glycerol solution and a control suspension comprising 100 non-desiccated nematodes in 20 µl of water were placed on a 1 cm diameter leaf disc in a 5 cm diameter Petri dish containing one filter paper (one leaf disc per dish). Thirty instar *T. ni* or *H. virescens* larvae were placed in each dish, which were then incubated at 25° C. Larval mortality was recorded after 48 hours. Data were corrected for control mortality and converted to percentages. Results showed no differences between the partially-desiccated nematode formulation and the control suspension in larval mortality for either insect species (FIG. 2). These results indicate that partially-desiccated nematodes suspended in a formulation having an Aw of 0.944 recover in the gut of the larvae, penetrate the hemocoel, release the symbiotic bacteria, and cause insect mortality equivalent to the fully-hydrated larvae within 48 hours. These results also demonstrate that partially-desiccated nematodes need not be re-hydrated prior to application to a plant.

Example 3

Survival and Pathogenicity of Partially-desiccated *Steinernema carpocapsae* Under Laboratory Conditions.

Figure 3:
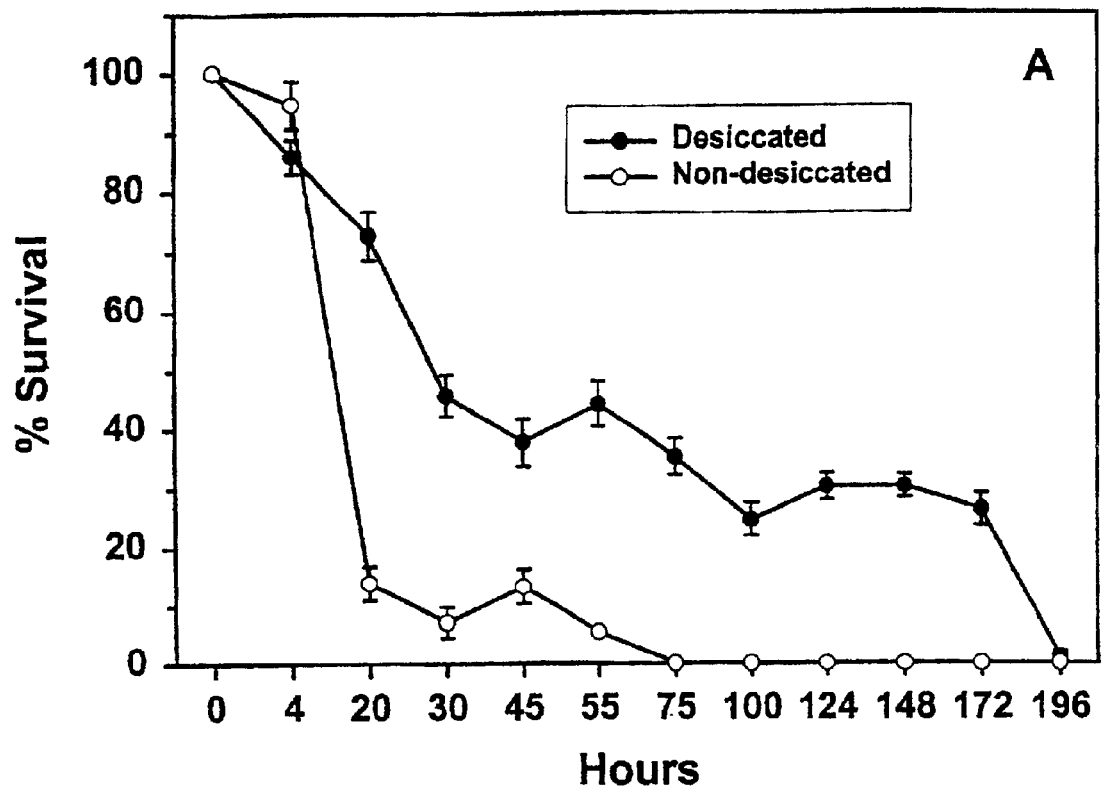
Figure 3:
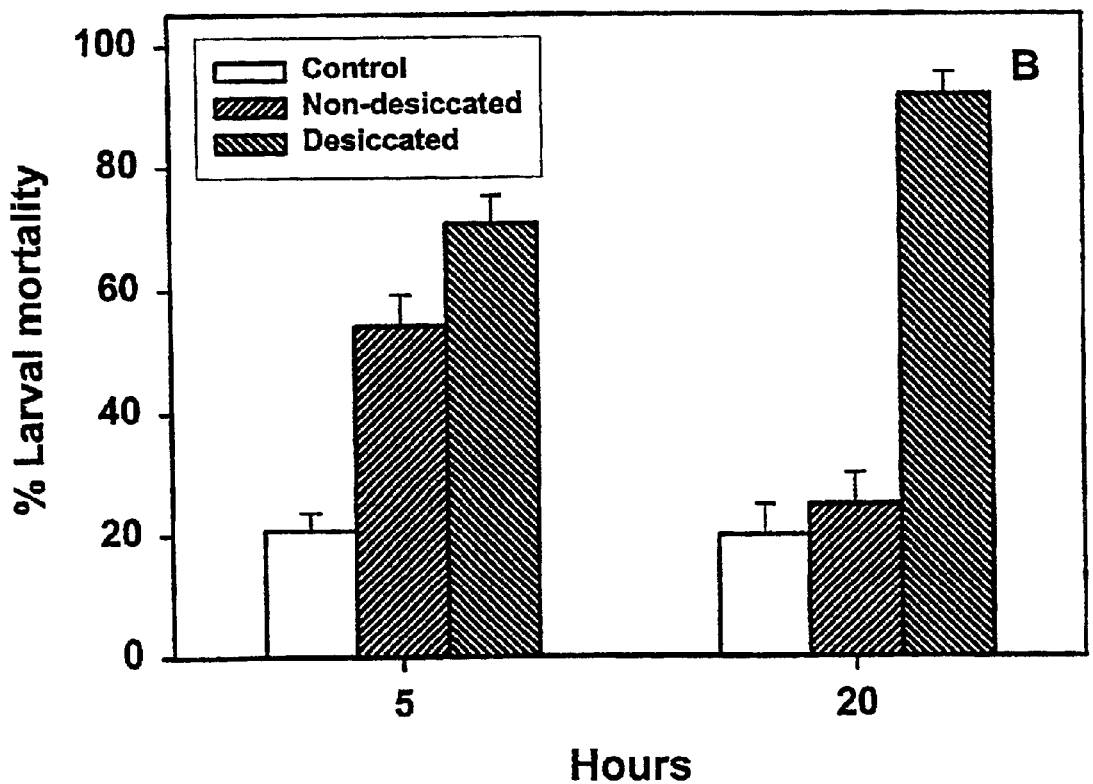

Infective juvenile *Steinernema carpocapsae* were partially-desiccated in 25% glycerol for two days prior to application (Aw=0.944). Control, fully-hydrated (i.e., non-desiccated) nematodes were also tested. The nematodes were applied to plants with a $CO_2$ pressurized hand sprayer. The non-desiccated nematodes were applied to plants in water and the partially-desiccated nematodes were applied in 25% glycerol solution. To determine nematode viability, leaves were collected from the plants, cut into 1 $cm^2$ pieces and viability was determined as described in Example 1 and the results are shown in FIG. 3A. The partially desiccated nematodes survived for 8 days at 80% relative humidity as compared to the fully-hydrated, i.e., non-desiccated, nematodes that survived for only 3 days. The survival of non-desiccated nematodes dropped to about 10% within the first 20 hours after applications to the foliage whereas the survival of the partially desiccated nematodes was over 70%. About 30% of the partially-desiccated nematodes survived for over 8 days.

To test pathogenicity of the partially desiccated nematodes and the non-desiccated nematodes, the 1 $cm^2$ pieces from the leaves were fed to the *T. ni* larvae and then survival of the larvae was determined. Partially-desiccated nematodes caused significantly higher mortality of the cabbage looper when the collected leaf discs were fed to the larvae (FIG. 3B). After 20 hours of exposure, the non-desiccated nematodes caused no larval mortality, but the desiccated nematodes caused 92% mortality.

Example 4

Figure 4:
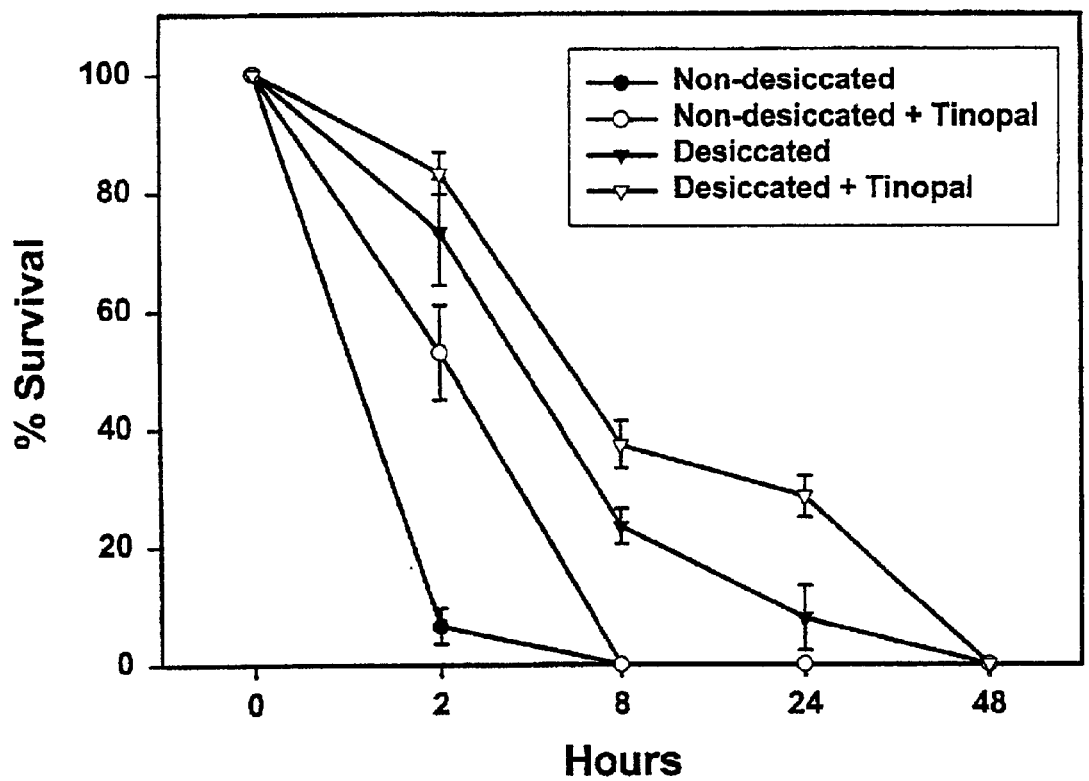
Figure 4:
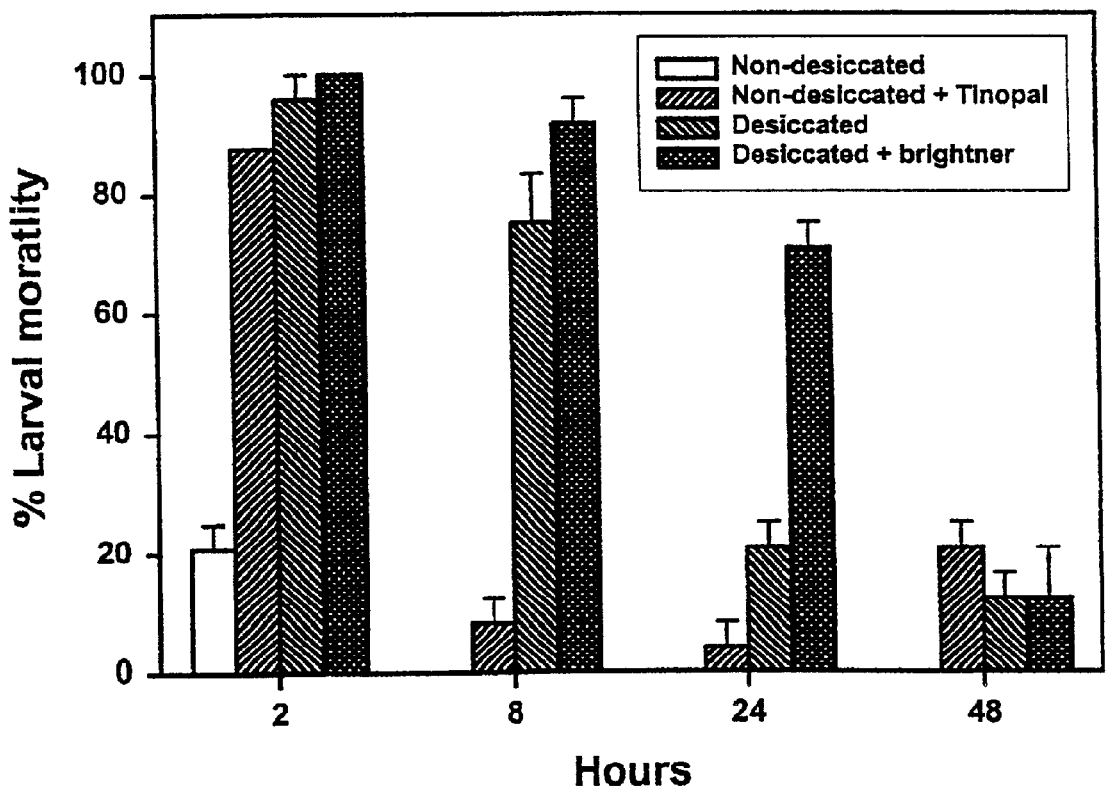

Survival and Pathogenicity of Partially-desiccated *Steinernema carpocapsae* Under Mini-field Conditions A glycerol containing formulation comprising partially-desiccated nematodes and having an Aw of 0.944 was prepared as described in Example 3. The formulation was applied to plants as described in Example 3. When indicated, Tinopal, a fluorescence brightener, was added to the partially-desiccated nematode formulation and the non-desiccated nematode water suspension before application to the plants. Viability of nematodes and of insect larvae that were fed the leaves were determined as in Example 3. In this example, survival of non-desiccated nematodes dropped below 5% within 2 hours as compared with 73% survival of the partially-desiccated nematodes (FIG. 4A). Tinopal improved survival of both the partially-desiccated and non-desiccated nematodes (53% and 83% for the non-desiccated and partially-desiccated nematodes, respectively). About 29% of the partially-desiccated nematodes survived 24 hours in the field with Tinopal and about 8% survived without Tinopal.

The surviving nematodes were infective and caused mortality of *T. ni* larvae fed on leaf discs obtained from the plants (FIG. 4B). Two hours after exposure to the plants, the non-desiccated nematodes caused only 20% larval mortality whereas the partially-desiccated nematodes caused 95% mortality (corrected for control mortality). The partially-desiccated nematodes also caused 92% and 78% larval mortality after 8 hours of exposure on the plants, and 75% and 23% mortality after 24 hours exposure of the nematodes on the plants with and without Tinopal, respectively.

Example 5

Tolerance to Heat of Partially-desiccated Nematodes Suspended in a Formulation of the Present Invention.

Figure 5:
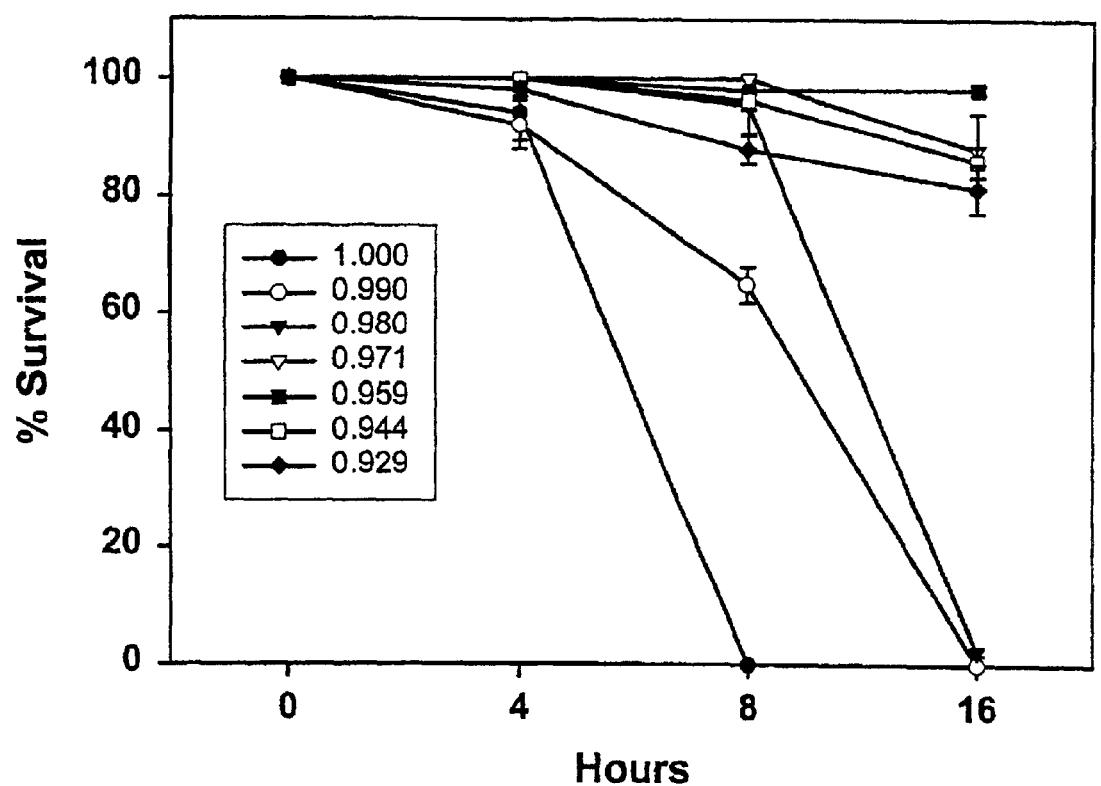

*Steinernema carpocapsae* were desiccated in various concentrations of glycerol for two days at a concentration of 5,000 nematodes per ml. Partially-desiccated and control, non-desiccated nematodes which had been suspended in water, were kept at 40° C. for different periods (FIG. 5). Samples (100 μl) were taken and nematode viability was determined after rehydration in 100 ml of water overnight. The partially-desiccated nematodes displayed enhanced tolerance to heat. Nematode survival depended on the level of desiccation and time of exposure. Maximum heat tolerance was obtained when the formulation comprising the partially desiccated nematodes had an Aw of 0.959.

Example 6

Ability of Partially-desiccated Nematodes to Withstand Additional, Rapid Desiccation Infective juvenile *Steinernema carpocapsae* were partially-desiccated in 25% glycerol for two days prior to exposure to additional desiccation in higher concentrations of glycerol (FIG. 6; A=30%, B=35%, C=40% and D=45%). The partially-desiccated nematodes showed significantly higher survival than the non-desiccated nematodes. For example, the survival of non-desiccated nematodes, which were then exposed to 45% glycerol (0.844 Aw), dropped below 5% within 9 days while the partially-desiccated nematodes, exposed to 45% glycerol, had 60% survival at 9 days.

Example 7

Effect of Extent of Nematode Desiccation on Insect Killing

Infective juvenile *Steinernema carposocapsae* were partially-desiccated in a solution comprising various concentrations of glycerol (shown as water activities in FIG. 7) for two days. Samples of each suspension comprising twenty nematodes were placed on a 1 cm² leaf disk and fed to a second instar *T ni* larva. Insect mortality was determined 3 days after the nematode suspensions were applied. The data show that nematodes having, an Aw of from 0.990 to 0.959 are most effective at killing the insect larvae. (FIG. 7).

What is claimed is:

1. A method of protecting plants from insects comprising: applying a formulation comprising partially-desiccated entomopathogenic nematodes and a carrier to plant surfaces growing above the surface of the ground, said formulation having a water activity of from about 0.94 to about 0.98, said carrier comprising water and at least one substance which maintains the water activity of the formulation at levels of from about 0.94 to about 0.98 when exposed to air at 70% relative humidity and 25° C. for 24 hours.

2. The method of claim 1, wherein the at least one substance is chosen from water-retentive polymers.

3. The method of claim 2, wherein the at least one substance is chosen from water-retentive polymers that are gel-forming polymers.

4. The method of claim 1, wherein the at least one substance is chosen from humectants.

5. The method of claim 4, wherein the humectant is chosen from glycerol, polyethylene glycol, soluble collagen, and sorbitol.

6. The method of claim 1, wherein the carrier comprises at least one water-retentive polymer and at least one humectant.

7. The method of claim 1, wherein the at least one substance is chosen from water-retentive polymers and the formulation further comprises an ultraviolet protectant.

8. The method of claim 1, wherein the at least one substance is chosen from humectants and the formulation further comprises an ultraviolet protectant.

9. The method of claim 6, wherein the formulation further comprises an ultraviolet protectant.

10. The method of claim 1, wherein the entomopathogenic nematodes are of the family Steinernematidae or Heterorhabditidae.

11. The method of claim 1, wherein the entomopathogenic nematodes are symbiotically associated with Enterobacteriaceae bacteria.

12. The method of claim 1, wherein the partially-desiccated entomopathogenic nematodes have enhanced survival after application to soil or plants as compared to entomopathogenic nematodes that have not been desiccated.

13. The method of claim 1, wherein the partially-desiccated entomopathogenic nematodes are third-stage infective juveniles.

14. The method of claim 1, wherein the entomopathogenic nematodes have been partially desiccated by placing said nematodes in environments of progressively-decreasing relative humidity or aqueous solutions of progressively-increasing concentrations of glycerol.

15. The method of claim 1, wherein the formulation is applied to foliage of the plant.

16. The method of claim 1, wherein the formulation is applied by spraying.

17. The method according to claim 1, wherein the at least one substance comprises at least one water-retentive polymer and at least one humectant.

18. A formulation for protecting plants from insects, comprising:
a) partially-desiccated entomopathogenic nematodes, and
b) a carrier comprising water and a substance for maintaining the water activity of the formulation at levels of from about 0.94 to about 0.98 when exposed to air at 70% relative humidity and 25° C. for 24 hours; and wherein said formulation is a liquid or gel.

19. The formulation of claim 16, wherein the substance is a water-retentive polymer, a humectant, or a combination of a water-retentive polymer and a humectant.

20. The formulation of claim 18, further comprising an ultraviolet protectant.

21. A formulation for protecting plants from insects, comprising:

a) partially-desiccated entomopathogenic nematodes having a water activity of between 0.950 and 0.980, and b) a carrier comprising water and a substance for maintaining the water activity of the formulation at levels between about 0.940 and 0.980 when exposed to air at 70% relative humidity and 25° C. for 24 hours, wherein said substance is a humectant or a water-retentive polymer or both; and wherein said formulation is a liquid or gel and has a water activity of from about 0.940 to about 0.980.

* * * * *